United States Patent [19]

Heins et al.

[11] 4,032,676
[45] June 28, 1977

[54] N-POLYHYDROXYALKYL-AMINO ACIDS, THEIR MANUFACTURE AND SKIN TREATING AGENTS CONTAINING THE SAME

[75] Inventors: Arnold Heins, Hilden; Hinrich Möller, Dusseldorf-Benrath; Rainer Osberghaus, Dusseldorf-Urdenbach, all of Germany

[73] Assignee: Henkel & Cie G.m.b.H., Dusseldorf-Holthausen, Germany

[22] Filed: Dec. 20, 1974

[21] Appl. No.: 534,805

[30] Foreign Application Priority Data

Dec. 24, 1973 Germany .......................... 2364525

[52] U.S. Cl. .............................. 424/273; 260/309; 260/326.14 T; 260/501.11; 260/518 R; 260/519; 260/534 E; 260/534 M; 260/534 R; 260/534 S; 424/170; 424/274; 424/307; 424/319; 424/326

[51] Int. Cl.² ...................................... A61K 31/415

[58] Field of Search ................ 424/319, 273, 326

[56] References Cited

UNITED STATES PATENTS 3,843,798 10/1974 Cook et al. .................. 424/319
3,860,648 1/1975 Diamond et al. ................ 424/319
3,867,539 2/1975 Henkin ........................ 424/319

Primary Examiner—Dale R. Ore
Attorney, Agent, or Firm—Hammond & Littell

[57] ABSTRACT

The present invention relates to N-polyhydroxyalkyl-amino acids of the formula

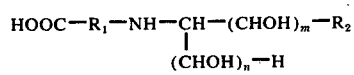

wherein $R_1$ represents a phenylene or a group of the general formula —$CHR_3$—, wherein $R_3$ represents hydrogen, alkyl, benzyl possibly substituted by a hydroxyl group, hydroxyalkyl, mercaptoalkyl, methylthioalkyl, aminoalkyl, polyhydroxylalkylaminoalkyl, carboxyalkyl, guanidinoalkyl, N-polyhydroxyalkylguanidinoalkyl or a ureidoalkyl group, $R_2$ represents a $CH_2OH$ or COOH group, m stands for the integers of 3 or 4 and n for the integer 0, if $m = 3$, when $R_2$ is COOH, or 4, or for the number 1, if $m = 3$ and $R_2$ represents a $CH_2OH$ group, their alkali metal salts or possibly substituted ammonium salts; as well as the process of preparing the same and skin care and protection agents containing an effective amount of said N-polyhydroxyalkyl-amino acids.

30 Claims, No Drawings

N-POLYHYDROXYALKYL-AMINO ACIDS, THEIR MANUFACTURE AND SKIN TREATING AGENTS CONTAINING THE SAME

OBJECTS OF THE INVENTION

An object of the present invention is the obtaining of N-polyhydroxyalkyl-amino acid compounds selected from the group consisting of (1) acids of the formula

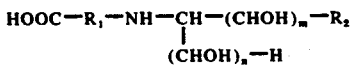

wherein $R_1$ is a member selected from the group consisting of phenylene and $-CHR_3-$, wherein $R_3$ is a member selected from the group consisting of hydrogen, alkyl having 1 to 6 carbon atoms, benzyl, hydroxybenzyl, hydroxyalkyl having 1 to 6 carbon atoms, mercaptoalkyl having 1 to 6 carbon atoms, methylthioalkyl having 1 to 6 carbon atoms in the alkyl, aminoalkyl having 1 to 6 carbon atoms, polyhydroxyalkylaminoalkyl having the formula

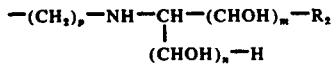

where $p$ is an integer from 1 to 6 and $m$, $n$ and $R_2$ have the following assigned values, carboxyalkyl having 1 to 6 carbon atoms in the alkyl, guanidinoalkyl having 1 to 6 carbon atoms in the alkyl, polyhydroxalkylquandinoalkyl having the formula

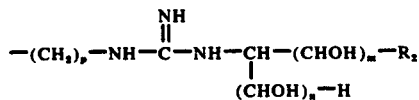

where $p$ has the above assigned values and $m$, $n$ and $R_2$ have the following assigned values, ureidoalkyl having 1 to 6 carbon atoms in the alkyl, and glyoxalinoalkyl having 1 to 6 carbon atoms in the alkyl; $R_2$ is a member selected from the group consisting of $-CH_2OH$ and $-COOH$, $m$ is an integer 3 or 4, and $n$ is an integer 0, or, when $m$ is 3 and $R_{2\ 2}$ is $-CH_2OH$, 1, (2) alkali metal salts thereof, (3) ammonium salts thereof and (4) lower alkylammonium and lower alkylolammonium salts thereof.

Another object of the present invention is the development of a process to produce the above N-polyhydroxyalkyl-amino acid compounds.

A yet further object of the present invention is the development of a cosmetic composition for the care and protection of the skin of warm-blooded aminals comprising from 2% to 20% by weight of at least one of the above N-polyhydroxyalkyl-amino acid compounds, and the remainder inert cosmetic excipients.

These and other objects of the present invention will become more apparent as the description thereof proceeds.

DESCRIPTION OF THE INVENTION

The above objects have been achieved by the discovery of N-polyhydroxyalkyl-amino acid compounds selected from the group consisting of (1) acids of the formula

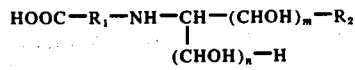

wherein $R_1$ is a member selected from the group consisting of phenylene and $-CHR_3-$, wherein $R_3$ is a member selected from the group consisting of hydrogen, alkyl having 1 to 6 carbon atoms, benzyl, hydroxybenzyl, hydroxyalkyl having 1 to 6 carbon atoms, mercaptoalkyl having 1 to 6 atoms, methylthioalkyl having 1 to 6 carbon atoms in the alkyl, aminoalkyl having 1 to 6 carbon atoms, polyhydroxyalkylaminoalkyl having the formula

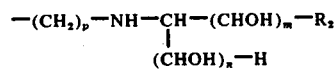

where $p$ is an integer from 1 to 6 and $m$, $n$ and $R_2$ have the following assigned values, carboxyalkyl having 1 to 6 carbon atoms in the alkyl, guanidinoalkyl having 1 to 6 carbon atoms in the alkyl, polyhydroxyalkyl-guanidoalkyl having the formula

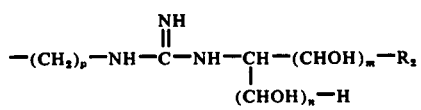

where $p$ has the above assigned values and $m$, $n$ and $R_2$ have the following assigned values, ureidoalkyl having 1 to 6 carbon atoms in the alkyl, and glyoxalinoalkyl having 1 to 6 carbon atoms in the alkyl; $R_2$ is a member selected from the group consisting of $-CH_2OH$ and $-CPOOH$, $m$ is an integer 3 or 4, and $n$ is an integer 0, or, when $m$ is 3 and $R_2$ is $-CH_2OH$, 1, (2) alkali metal salts thereof, (3) ammonium salts thereof and (4) lower alkylammonium and lower alkylolammonium salts thereof.

The compounds in accordance with the invention are colorless to slightly yellow colored crystalline, oily, wax-like or resin-like substances which are distinguished by a high capacity to absorb water and by an excellent capacity for water retention. Owing to these properties and their good physiological compatibility they are highly suitable as skin humectants in cosmetic preparations, in particular in agents for the case and protection of the skin.

The manufacture of the N-polyhydroxyalkl-amino acids in accordance with the invention takes place by the reductive catalytic amination of monosaccharides and their corresponding uronic acids having from 5 to 6 carbon atoms, with amino acids of the general formula:

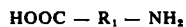

wherein $R_1$ has the meaning as indicated above. The catalyst is preferably a hydrogenation catalyst, in particular Raney nickel, palladium on activated carbon or copper chromite. Preferred solvents are alcohols, cyclic ethers, oligo ethers, and their mixtures with water. More particularly, the solvents are preferentially alkanols having 1 to 3 carbon atoms, alkanediols having 2 to 4 carbon atoms, alkanetriols having 3 to 5 carbon atoms, dioxane, tetrahydrofuran, polyoxyalkylene glycols having 2 to 3 carbon atoms in the alkylene and 1 to 3 ether oxygen atoms and their mixtures with water. The reaction is carried out at a temperature of between 50° C and 100° C. The molar ratio of monosaccharide or its corresponding uronic acid to amino acid is 1:1 when the amino acid contains only one amino group. In several amino groups are presemt in the amino acid the molar ratio may be increased correspondng to their number. From the reaction products, the N-polyhydroxyalkyl-amino acids can be recovered by distilling off the solvent and possibly recrystallizing from an alkanol/water mixture.

More particularly, the process of the invention is a process for the production of the above N-polyhydroxyalkyl-amino acid compounds consisting essentially of subjecting a solution of a carbohydrate having from 5 to 6 carbon atoms selected from the group consisting of monosaccharides and their corresponding uronic acids and an amino acid having the formula

wherein $R_1$ is a member selected from the group consisting of phenylene and $-CHR_3-$, wherein $R_3$ is a member selected from the group consisting of hydrogen, alkyl having 1 to 6 carbon atoms, benzyl, hydroxybenzyl, hydroxyalkyl having 1 to 6 carbon atoms, mercaptoalkyl having 1 to 6 carbon atoms, methylthioalkyl having 1 to 6 carbon atoms in the alkyl, aminoalkyl having 1 to 6 carbon atoms, polyhydroxyalkylaminoalkyl having the formula

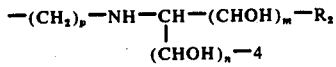

where $p$ is an integer from 1 to 6 and $m$, $n$ and $R_2$ have the previously assigned values, carboxyalkyl having 1 to 6 carbon atoms in the alkyl guanidinoalkyl having 1 to 6 carbon atoms in the alkyl, polyhydroxyalkylguanidinoalkyl having the formula

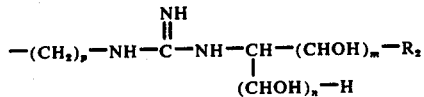

where $p$ has the above assigned values and $m$, $n$ and $R_2$ have the peviously assigned values, ureidoalkyl having 1 to 6 carbon atoms in the alkyl, and glyoxalinoalkyl having 1 to 6 carbon atoms in the alkyl, in substantially equimolar amounts based on the number of amino groups in said amino acid, in a water-miscible inert organic solvent and optionally water, to a reductive catalytic amination in the presence of hydrogen and a hydrogenation catalyst at a temperature of from 50° C to 100° C, and recovering said N-polyhydroxyalkyl-amino acid compounds.

For the manufacture of the compounds in accordance with the invention a solution of hexoses, pentoses or the corresponding uronic acids in alcohols, cyclic ethers, or oligo ethers or their mixtures with water are reductively aminated at a temperature between 50° to 100° C in the presence of hydrogenation catalysts under a hydrogen pressure of 1 to 200 kg/cm² with amino acids of the general formula

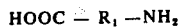

wherein $R_1$ has the above mentioned meaning, in the molar ratio of amino acid to monosaccharide or uronic acid equal to 1:1 or 1:$p$, $p$ being the number of the amino groups or reactive nitrogen functions in the amino acid molecule. The reaction solutions, after removal by filtration of the catalyst, are evaporated and the N-polyhydroxyalkylamino acids obtained are possibly recrystallized from an alkanol/water mixture.

Suitable hexoses, pentoses or uronic acids for the manufacture of the compounds in accordance with the invention are for example glucose, mannose, gulose, galactose, fructose, sorbose, xylose, arabinose, ribose, glucuronic acid, galacturonic acid and mannuronic acid.

Amino acids suitable for the manufacture of the compounds wherein according with the invention are for example glycine, alanine, serine, cystine, cysteine, lanthionine, phenylalanine, tyrosine, tryptophane, histidine, α-aminobutyric acid, methionine, valine, norvaline, leucine, isoleucine, norleucine, arginine, ornithine, lysine, aspartic acid, glutamic acid, threonine, hydroxy-glutamic acid, citrulline and p-amino-benzoic acid.

The new compound produced in accordance with the invention are for example: N-(2,3,4,5,6-pentahydroxyhexyl)-glycine, N-(2,3,4,5,6-pentahydroxy-hexyl)-DL-α-alanine, N-(2,3,4,5,6-pentahydroxy-hexyl)-DL-serine, N-(2,3,4,5,6-pentahydroxy-hexyl)-L-(+)-aspartic acid, N-(2,3,4,5,6-pentahydroxy-hexyl)-L-(+)-arginine, N,N'-di(2,3,4,5,6-pentahydroxy-hexyl)-L-(+)-arginine, N-(2,3,4,5,6-pentahydroxy-hexyl)-L-(+)-glutamic acid, N-(2,3,4,5,6-pentahydroxy-hexyl)-L-(−)-histidine, N-(2,3,4,5,6-pentahydroxy-hexyl)-DL-threonine, N-(2,3,4,5,6-pentahydroxyhexyl)-DL-methionine, N-(2,3,4,5,6-pentahydroxy-hexyl)-L-)+)-citrulline, N,N'-di(2,3,4,5,6-pentahydroxy-hexyl)-L-(+)-lysine, N-(2,3,4,5,6-pentahydroxy-hexyl)-L-(−)-tyrosine, N-(2,3,4,5,6-pentahydroxy-hexyl)-L-(+)-lysine, N-(2,3,4,5-tetrahydroxy-pentyl)-L-(+0-glutamic acid, N-(5-carboxy-2,3,4,5-tetrahydroxy-pentyl)-L-(−)-histidine, N-(5-carboxy-2,3,4,5-tetrahydroxy-pentyl)-L-(+)-citrulline, N-(5-carboxy-2,3,4,5-tetrahydroxy-pentyl)-L-(+)-glutamic acid, N-(2,3,4,5-tetrahydroxy-penyl)-L-(+)-citrulline, N-(2,3,4,5-tetrahydroxy-pentyl-L-(−)-tyrosine, N-(2,3,4,5,6-pentahydroxy-hexyl)-p-amino-benzoic acid, N-(1,3,4,5,6-pentahydroxy-2-hexyl)-L-(+)-glutamic acid, N-(1,3,4,5,6-pentahydroxy-2-hexyl)-DL-serine and N-(2,3,4,5,6-pentahydroxy-hexyl)-L-(+)-cysteine.

The compounds in accordance with the invention are colorless to slightly yellow colored crystalline, oily, wax-like or resin-like substances which are distinguished by a high capacity to absorb water and by an excellent capacity for water retention. Owing to these properties and their good physiological compatibility they are highly suitable as skin humectants in cosmetic preparations, in particular in agents for the care and protection of the skin.

For this application in cosmetic preparations a special purification or processing of the reaction products obtained after the removal by filtration of the hydrogenation catalyst is not required, so that the substances to be incorporated in the cosmetic may, as a consequence of their manufacture, contain approximately from 0.1% to 10% by weight of hexites or pentites (from the monosaccharides used) or onic-acids (from the uronic acids used) and 0.1% to 10% by weight of unreacted amino acids. The presence of such impurities has no influence whatever on the usability of the product as skin humectants in cosmetic preparation.

It is known that in addition to other factors a certain hygroscopicity is necessary for the protection of a healthy skin. If the skin is deprived of the substances which are responsible for this hygroscopicity as well as its continual restoration by environmental circumstances such as repeated washings, effect of chemicals or strong weather influences, alterations occur in the stratum corneum, as a result of which the protective effect of the skin against harmful influences on the environment may be considerably diminished.

It was found that the functional capacity of the skin may be maintained or restored even to a higher degree than before if it is treated with agents for the care and protection of the skin, which besides the customary constituents include from 2% to 20% by weight, preferably 5% to 15% by weight, based on the total composition, of the N-polyhydroxyalkyl-amino acids in accordance with the invention, as well as their alkali metal, ammonium and substituted ammonium salts.

It is well known that by themselves, monosaccharides as well as amino acids, may be added to skin preparations. Agents for the care and protection of skin containing reducing sugars and amino acids in aqueous medium are also known. The advantage of the agents for the care and protection of skin having a content of the N-polyhydroxyalkyl-amino compounds in accordance with the invention over the known agents consists in their deep penetration into the skin and in their ability to keep the skin moist and elastic due to their excellent water absorption and water retention capacity, so that the skin can exercise to an increased degree its natural protective action. A further advantage of the agents for the care and protection of skin in accordance with the invention is their color stability, in contrast to agents with a content of reducing sugars and amino acids, where a brownish discoloration gradually develops in the course of prolonged storage.

Among the compositions for the care and protection of the skin having special skin-caring properties due to the addition of the N-polyhydroxyalkyl-amino acids in accordance with the invention or their salts with alkali metals, ammonium ions, alkanolamines, etc. are emulsions of oil-in-water or water-in-oil type. These are the conventional day creams, night creams and nourishing creams, baby creams, cleaning creams, cold creams, skin protection creams, glycerol creams, creams with special additives of animal or vegetable origin, sun protection or sun tanning creams, and sun protection emulsions, face lotions and after-shave lotions. The incorporation of the agents for care and protection of the skin may take place in the known manner by simple stirring-in or dissolving. In addition to the N-polyhydroxyalkyl-amino acids in accordance with the invention, the cosmetic preparations may contain the constituents normally present in them such as emulsifiers, fatty substances, plant extracts, preservatives, perfumes and solvents in the customary amounts. The pH value of the agents for the care and protection of the skin may be in the acid to neutral region (pH 5 – 7.0) and is appropriately adjusted to weakly acid values of about pH 6.

The following examples are intended to illustrate the subject of the invention without, however, limiting it to these examples.

EXAMPLES

In the first place, the manufacture of some of the N-polyhydroxyalkyl-amino acids in accordance with the invention are described below.

EXAMPLE A

N-(2,3,4,5,6-pentahydroxy-hexyl)-glycine (N-carboxymethylglucamine)

A solution of 39.6 gm of D-glucose in 200 ml of water and 150 ml of methanol was added to a solution of 15 gm (0.2 mol) of glycine in 200 ml of water and 100 ml of methanol in an autoclave. Then, after the addition of 18.0 gm of Raney nickel, a hydrogenation was carried out in the autoclave with stirring at a pressure of 180 to 200 kg/cm$^2$. The autoclave was heated in a progressive manner first for 2 hours to 50° C, subsequently for 2 hours to 70° C and finally for 2 hours to 90° C. After separation of the catalyst by filtration and evaporation of the reaction solution in vacuum, the highly viscous residue obtained was allowed to stand for a few days. After recrystallization had commenced the same was completed by crystallization from 100 ml of boiling methanol. 35 gm (73% of theory) of N-(2,3,4,5,6-pentahydroxy-hexyl)-glycine having a melting point of 172° to 177° C (decomposition) were obtained. An analytically pure sample recrystallized from water/2-propanol melted at 175° to 180° C with decomposition.

N-(2,3,4,5,6-pentahydroxy-hexyl)-glycine or N-carboxymethyl-glucamine was obtained in the same good yield and purity using 10 gm of palladium on activated carbon (10%) instead of Raney nickel as a catalyst, the remaining experimental conditions being the same.

The following compounds were obtained in analogous manner.

EXAMPLE B

N-(2,3,4,5,6-pentahydroxy-hexyl)-DL-α-alanine

The product was made from D-glucose and DL-α-alanine using Raney nickel or palladium/activated carbon (10%) as a catalyst. The melting point of the compound was at 225° to 226° C with decomposition.

EXAMPLE C

N-(2,3,4,5,6-pentahydroxy-hexyl)-DL-serine

The product was made from D-glucose and L-(−)-serine. Raney nickel or palladium/activated carbon (10%) were used as catalysts. The melting point of the compound was at 202° C with decomposition.

EXAMPLE D

N-(2,3,4,5,6-pentahydroxy-hexyl)-L-(+)-aspartic acid, mono sodium salt.

The product was made from D-glucose and L-(+)-aspartic acid, mono sodium salt using Raney nickel or palladium/activated carbon (10%) as a catalyst. The compound melted at 89° to 90° C.

EXAMPLE E

N-(2,3,4,5,6-pentahydroxy-hexyl)-L-(+)-aspartic acid.

The product was made from D-glucose and L-(+)-aspartic acid using palladium /activated carbon (10%) as a catalyst and yielded a yellowy, wax-like product.

EXAMPLE F

N-(2,3,4,5,6-pentahydroxy-hexyl)-L-(+)-arginine

The starting materials were D-glucose and L-(+)-arginine. The reductive amination was carried out using Raney nickel or palladium/activated carbon (10%) as a catalyst in the temperature range from 50° to 70° C and yielded a colorless, resin-like product.

EXAMPLE G

N,N'-di-(2,3,4,5,6-pentahydroxy-hexyl)-L-(+)-arginine

The manufacture took place by reductive animation of D-glucose and L-(+)-arginine in the molar ratio 2:1 using Raney nickel or palladium/activated carbon (10%) as a catalyst in the temperature range from 50° to 70° C. As a reaction product a light-yellow resin was obtained.

EXAMPLE H

N-(2,3,4,5,6-pentahydroxy-hexyl)-L-(+)-glutamic acid

The product was made from D-glucose and L-(+)-glutamic acid using Raney nickel or palladium/activated carbon (10%) as a catalyst. The product had a melting point of 94° C and an $R_F$-value of 0.61 (determined on DC-finished plates of silica gel G (Merck) with a transporting fluid made up of 85 parts by volume of methanol and 15 parts by volume of water).

EXAMPLE J

N-(2,3,4,5,6-pentahydroxy-ethyl)-L-(−)-histidine

The manufacture took place from D-glucose and L-(−)-histidine using palladium/activated carbon (10%) as a catalyst and yielded a product having a melting point of 165° to 170° C (decomposition).

EXAMPLE K

N-(2,3,4,5,6-pentahydroxy-hexyl)-DL-threonine

The starting materials were D-glucose and DL-threonine. The reductive amination was carried out using Raney nickel or palladium/activated carbon (10%) and yielded a product having a melting point of 219° C (decomposition) and a $R_F$-value of 0.67 (determined on DC-finished plates of silica gel G (Merck) with a transporting fluid made up to 75 parts by volume of methanol and 25 parts by volume of water).

EXAMPLE L

N-(2,3,4,5,6-pentahydroxy-hexyl)-DL-methionine

The product was made from D-glucose and DL-methionine using Raney nickel or palladium/activated carbon (10%) as a catalyst. The compound had a melting point of 245° C (decomposition) and an $R_F$-value of 0.71 (determined as indicated in Example K).

EXAMPLE M

N-(2,3,4,5,6-pentahydroxy-hexyl)-L-(+)-citrulline

The product was made from D-glucose and L-(+)-citrulline using Raney nickel or palladium/activated carbon as a catalyst and heating for 2 hours to 50° C and 4 hours to 70° C. A product was obtained which had a melting point of 176° C and an $R_F$-value of 0.7 (determined on DC-finished plates of silica gel G (Merck) with a transporting liquid made up of 50 parts by volume of methanol and 50 parts by volume of water).

EXAMPLE N

N,N'-di-(2,3,4,5,6-pentahydroxy-hexyl)-L-(+)-lysine

The starting materials were D-glucose and L-(+)-lysine in a molar ratio 2:1. The reductive amination took place using Raney nickel or palladium/activated carbon (10%) as a catalyst and heating for 2 hours to 50° C and 4 hours to 70° C, a yellowish resin-like product being obtained.

EXAMPLE O

N-(2,3,4,5,6-pentahydroxy-hexyl)-L-(−)-tyrosine

The product was made from D-glucose and L-(−)-tyrosine using Raney nickel or palladium/activated carbon as a catalyst under the conditions of the previous example and a colorless, resin-like product was obtained which had an $R_F$-value of 0.70 (determined on DC-finished plates of silica gel G (Merck) with a transporting liquid made up of 50 parts by volume of methanol, 50 parts by volume of water and 2 parts by volume of glacial acetic acid).

EXAMPLE P

N-(2,3,4,5,6-pentahydroxy-hexyl)-L-(+)-lysine

The starting materials were D-glucose and L-(+)-lysine in the molar ratio 1:1. The reductive amination took place using palladium/activated carbon (10%) as a catalyst under the conditions of the above examples and yielded a colorless, wax-like product.

EXAMPLE Q

N-(2,3,4,5-tetrahydroxy-pentyl)-L-(+)-glutamic acid

The product was made from D-ribose and L-(+)-glutamic acid using Raney nickel as a catalyst under the conditions of the above examples. A resin-like product was obtained with a $R_F$-value of 0.80 (determined as indicated under Example M).

EXAMPLE R

N-(5-carboxy-2,3,4,5-tetrahydroxy-pentyl)-L-(−)-histidine, mono sodium salt

The product was made from the sodium salt of D-glucoronic acid and L-(−)-histidine using Raney nickel as a catalyst with heating for 2 hours to 50° C and 4 hours to 70° C. The reaction product was a brownish resin.

EXAMPLE S

N-(5-carboxy-2,3,4,5-tetrahydroxy-pentyl)-L-(+)-citrulline

The product was made from D-glucuronic acid and L-(+)-citrulline using Raney nickel as a catalyst under the conditions of the above example. A brownish, highly viscous oil was obtained.

EXAMPLE T

N-(5-carboxy-2,3,4,5-tetrahydroxy-pentyl-L-(+)-glutamic acid to 50° C

As starting material D-glucuronic acid and L-(+)-glutamic acid were used. The reductive amination was carried out using Raney nickel as a catalyst and heating for 2 hours C and for 4 hours to 70° C. The product obtained had a melting point of 90° C (with sintering)

and a $R_F$-value of 0.70 (determined on DC-finished plates of silica gel G (Merck) with a transporting liquid made up of 70 parts by volume of methanol and 30 parts by volume of water).

EXAMPLE U

N-(2,3,4,5-tetrahydroxy-pentyl)-L-(+)-citrulline

The product was made from D-ribose and L-(+)-citrulline using Raney nickel as a catalyst and heating for 2 hours to 50° C and for 4 hours to 70° C. The product obtained had a melting point of 172° to 175° C (decomposition) and an $R_F$-value of 0.52 (determined as indicated under Example T).

EXAMPLE V

N-(2,3,4,5-tetrahydroxy-pentyl)-L-(−)-tyrosine

The product was made from D-ribose and L-(−)-tyrosine using Raney nickel as a catalyst and heating for 2 hours to 50° C and for 4 hours to 70° C. The reaction product was yellowish, wax-like mass with an $R_F$-value of 0.65 (determined as indicated under Example M).

EXAMPLE W

N-(2,3,4,5,6-pentahydroxy-hexyl)-p-amino-benzoic acid

As starting materials D-glucose and p-amino-benzoic acid were used. The reductive amination was carried out using Raney nickel as catalyst and heating for 2 hours to 50° C and for 3 hours to 70° C. The product obtained had a melting point of 111° to 112° C.

EXAMPLE X

N-(1,3,4,5,6-pentahydroxy-2-hexyl)-L-(+)-glutamic acid

The product was made from D-fructose and L-(+)-glutamic acid using Raney nickel as a catalyst and heating for 2 hours to 50° C and for 33 hours to 70° C. The reaction product had a melting point of 149° C (decomposition) and an $R_F$-value of 0.62 (determined as indicated under Example T).

EXAMPLE Y

N-(1,3,4,5,6-pentahydroxy-2-hexyl)-DL-serine

The product, obtained in the form of a resin, was made from D-fructose and DL-serine using Raney nickel as a catalyst and heating for 2 hours to 50° C and for 3 hours to 70° C.

EXAMPLE Z

N-(2,3,4,5,6-pentahydroxy-hexyl)-L-(+)-cysteine

The product was made from D-glucose and L-(+)-cysteine using palladium/activated carbon as a catalyst and a yellowish, resin-like product was obtained.

In order to obtain salts of the above-mentioned N-polyhydroxy-alkyl-amino acids with alkali metals, ammonia, mono, di and triethanolamine or the trimethylethanol-ammonium ion, aqueous solutions of the N-polyhydroxyalkylamino acids were treated with the equimolar quantities of the corresponding base and evaporated in vacuum. For many purposes the aqueous solutions of the N-polyhydroxyalkylamino acids or of their salts may be used directly.

The determination of the water absorption capacity of the compounds in accordance with the invention took place by measuring the increase in weight during storage at 100% relative atmospheric moisture over a certain period of time, usually 48 hours. This was reported as mg water absorbed per 100 mg substance.

The water retention capacity was determined by measuring the residual water content of a moistened sample after storage at 0% relative moisture under a pressure of 12 mm Hg during a period of 45 minutes, 1½ hours and 8 hours. The moistening was made with 300 mg $H_2O$ per 100 mg substance. The residual water content was reported as mg of water per 100 mg of compound. The measured values listed in the following Table I were obtained.

TABLE I

Water retention and water absorption capacity of N-polyhydroxyalkyl-amino acids

| Product | Water retention in mg/100 mg substance | | | Water absorption in mg/100 mg substance after 48 hours or the number of hours indicated | |
|---|---|---|---|---|---|
| | after 45 min. | after 90 min. | after 8 hrs. | | |
| A | 10.2 | 6.3 | 3.6 | 43.6 | after 31.5 hours |
| B | 5.0 | — | — | 6.8 | after 7.5 hours |
| C | 6.3 | 2.1 | — | 84.5 | |
| P | 10.0 | 0.2 | — | 148.9 | |
| E | 69.0 | 30.9 | 13.6 | 89.3 | |
| H | 14.0 | 11.9 | 8.0 | 107.5 | after 28 hours |
| Z | — | — | — | 41.7 | after 28 hours |
| M | 38.7 | 27.7 | 14.4 | 123.0 | |
| O | 28.5 | 21.9 | 13.3 | 113.0 | |
| J | 88.5 | 23.3 | 12.6 | 102.8 | |
| L | 0.3 | — | — | 93.2 | |
| G | 14.7 | 12.5 | 9.2 | 91.6 | |
| K | 23.4 | 17.1 | 13.5 | 86.4 | |
| N | 8.9 | 8.0 | 6.2 | 115.5 | |
| D | 38.6 | 25.1 | 14.4 | 240.6 | |
| A triethanolamine salt | 19.5 | 14.5 | 6.8 | 115.0 | |
| A Na salt | 21.3 | 16.0 | 7.9 | 144.0 | |
| G Na salt | 55.7 | 20.0 | 14.2 | 186.7 | |
| L triethanolamine salt | 12.6 | — | — | 118.8 | |
| K Na salt | 21.0 | 12.8 | 9.4 | 223.3 | |
| E mono-triethanolamine salt | 8.9 | 6.9 | 4.8 | 188.6 | |
| M triethanolamine salt | 21.1 | 12.8 | 4.0 | 90.7 | |
| Z triethanolamine salt | 22.5 | 12.0 | 6.6 | 87.0 | |
| B Na salt | 21.4 | 12.4 | 6.5 | 207.5 | |
| B triethanolamine salt | 6.2 | 0.5 | — | 173.5 | |
| J Na salt | 29.5 | 22.0 | 17.3 | 161.8 | |
| J triethanolamine salt | — | — | — | 113.6 | |
| O Na salt | 94.7 | 12.7 | 10.2 | 186.3 | |
| O triethanolamine salt | 29.2 | 14.7 | 6.8 | 175.8 | |
| C Na salt | 14.5 | 13.5 | 11.0 | 319.8 | |

TABLE I-continued
Water retention and water absorption capacity of N-polyhydroxyalkyl-amino acids

| Product | Water retention in mg/100 mg substance | | | Water absorption in mg/100 mg substance after 48 hours or the number of hours indicated |
|---|---|---|---|---|
| | after 45 min. | after 90 min. | after 8 hrs. | |
| C triethanolamine salt | 18.2 | 11.9 | 7.4 | 171.1 |
| L Na salt | 29.1 | 21.4 | 15.5 | 178.4 |
| K triethanolamine salt | 23.7 | 15.0 | 8.6 | 125.7 |
| F triethanolamine salt | 23.1 | 14.5 | 8.0 | 150.7 |
| H Na salt | 71.9 | 56.2 | 17.2 | 173.5 |
| H triethanolamine salt | 15.0 | — | . | 201.0 |
| M Na salt | 21.6 | 17.4 | 12.7 | 166.1 |
| Z Na Salt | 6.4 | 4.7 | 2.4 | 92.3 |
| X | 25.9 | 19.9 | 15.0 | 101.4 |
| Y | 13.2 | 10.4 | 6.2 | 76.4 |
| X mono-Na salt | 15.9 | 13.7 | 11.6 | 190.3 |
| X di-Na salt | 36.4 | 26.0 | 20.7 | 264.4 |
| X mono-triethanolamine salt | 10.5 | 8.4 | 6.3 | 152.4 |
| Y Na salt | 18.6 | 16.1 | 11.1 | 143.4 |
| Y triethanolamine salt | 26.1 | 15.5 | 8.5 | 204.9 |
| T | 15.8 | 11.2 | 8.6 | 116.9 |
| S | 23.8 | 17.2 | 13.8 | 93.4 |
| R | 26.4 | 18.1 | 11.3 | 96.1 |
| T tri-Na salt | 36.8 | 25.1 | 19.1 | 172.2 |
| T tri-triethanolamine salt | 17.2 | 11.9 | 7.2 | 212.6 |
| Q | 10.6 | 0.2 | — | 74.0 |
| V | 16.6 | 9.0 | 4.7 | 124.7 |
| U | 9.2 | 0.1 | — | 51.3 |

"—" means: not measured.

The above Table indicates, beside the strong hygroscopicity, also the remarkable water retention capacity of the compounds in accordance with the invention, in particular when the compounds are in the form of their sodium or triethanolamine salts.

In the following, we will give a few examples of cosmetic preparations containing substances in accordance with the invention as skin humectants.

EXAMPLE 1

| Day cream, slightly greasy | Parts by Weight |
|---|---|
| Fatty acid partial glyceride Cutina MD Dehydag | 6.0 |
| Stearic acid | 8.0 |
| Mixture of nonionic emulsifiers Eumulgin C 700 Dehydag | 3.0 |
| 2-octyl-dodecanol | 4.0 |
| Vegetable oil | 3.0 |
| Paraffin oil | 3.0 |
| Triethanolamine | 0.4 |
| 1,2-propylene glycol | 3.0 |
| Product G, sodium salt | 8.0 |
| Nipagin M | 0.2 |
| Perfume oil | 1.0 |
| Water | 60.4 |

EXAMPLE 2

| Baby cream | Parts by Weight |
|---|---|
| Mixture of higher molecular esters, mainly mixed esters of pentaerythritol fatty acid ester and citric acid fatty alcohol ester Dehymuls L Dehydag | 7.0 |
| Decyl oleate | 10.0 |
| Vaseline | 10.0 |
| Wool fat | 5.0 |
| Boric acid | 0.2 |
| Talcum | 12.0 |
| Zinc oxide | 8.0 |
| Nipagin M | 0.2 |
| Product T, tri-sodium salt | 12.0 |
| Water | 35.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |
| Wool fat | 2.0 |
| Glycerol | 1.0 |
| Product D | 10.0 |
| Nipagin M | 0.2 |
| Perfume Oil | 1.0 |
| Water | 56.8 |

EXAMPLE 4

| Boro-glycerol cream | Parts by Weight |
|---|---|
| Colloidally dispersed mixture of 90 parts of cetyl/stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M | 0.2 |
| Product X, di-sodium salt | 15.0 |
| Water | 29.8 |

EXAMPLE 5

| Sun protection cream | Parts by Weight |
|---|---|
| Mixture of higher molecular esters with fatty substances Dehymuls K Dehydag | 30.0 |
| Decyl oleate | 15.0 |
| Light protection agent | 5.0 |
| Nipagin M | 0.2 |
| Product M | 10.0 |
| Water | 39.8 |

EXAMPLE 6

| Face mask | Parts by Weight |
|---|---|
| Mixtures of fatty acid partial glyceride with emulsifiers Cutina LE Dehydag | 12.0 |
| Decyl oleate | 4.0 |
| Vitamin oil | 5.0 |
| Kaolin | 2.0 |
| Rice starch | 3.0 |
| Nipagin M | 0.2 |
| Product Y, triethanolamine salt | 12.0 |
| Water | 61.8 |

EXAMPLE 7

| After-shave lotion | Parts by Weight |
|---|---|
| Oleyl/cetyl alcohol | 1.0 |
| Ethanol 96% | 67.5 |
| Menthol | 0.2 |
| Camphor | 0.2 |
| Peru balsam | 0.1 |
| Perfume | 0.5 |
| Hamamelis extract | 10.0 |
| Boric acid | 0.5 |
| Product J, sodium salt | 10.0 |
| Water | 10.0 |

EXAMPLE 8

| Face lotion | Parts by Weight |
|---|---|
| Cucumber essence | 15.0 |
| Citric acid | 0.2 |
| Ethanol 96% | 15.0 |
| Product C, sodium salt | 10.0 |
| Perfume | 1.0 |
| Water | 58.8 |

In place of the compounds in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A cosmetic moisturing composition for the care and protection of the skin of warm-blooded animals consisting essentially of an emulsion adjusted to a pH between 5 and 7 containing an emulsifier, from 2% to 20% by weight of at least one N-polyhydroxyalkyl-amino acid compound selected from the group consisting of (1) acids of the formula

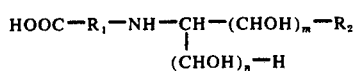

wherein $R_1$ is $-CHR_3-$, wherein $R_3$ is a member selected from the group consisting of hydrogen, alkyl having 1 to 6 carbon atoms, hydroxyalkyl having 1 to 6 carbon atoms, mercaptoalkyl having 1 to 6 carbon atoms, methylthioalkyl having 1 to 6 carbon atoms in the alkyl, aminoalkyl having 1 to 6 carbon atoms, polyhydroxyalkylaminoalkyl having the formula

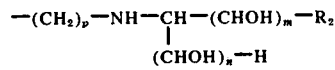

where $p$ is an integer from 1 to 6, and $m$, $n$ and $R_2$ have the following assigned values, carboxyalkyl having 1 to 6 carbon atoms in the alkyl, guanidinoalkyl having 1 to 6 carbon atoms in the alkyl, polyhydroxyalkyl-guanidinoalkyl having the formula

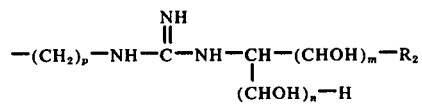

where $p$ has the above-assigned values and $m$, $n$ and $R_2$ have the following assigned values, ureidoalkyl having 1 to 6 carbon atoms in the alkyl and glyoxalinoalkyl having 1 to 6 carbon atoms in the alkyl, $R_2$ is a member selected from the group consisting of $-CH_2OH$ and $-COOH$, $m$ is an integer 3 or 4, and $n$ is 0, or, when $m$ is 3 and $R_2$ is $-CH_2OH$, $n$ is 1, (2) alkali metal salts thereof, (3) ammonium salts thereof and (4) lower alkylammonium and lower alkylol ammonium salts thereof, and the remainder inert cosmetic excipients, said emulsion being selected from the group consisting of oil-in-water emulsions and water-in-oil emulsions.

2. A cosmetic moisturizing composition consisting essentially of a water and ethanol solution adjusted to a pH between 5 and 7 containing from 2% to 20% by weight of at least one N-polyhydroxyalkyl-amino acid compound selected from the group consisting of (1) acids of the formula

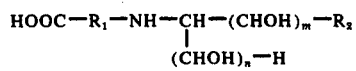

wherein $R_1$ is $-CHR_3-$, wherein $R_3$ is a member selected from the group consisting of hydrogen, alkyl having 1 to 6 carbon atoms, hydroxyalkyl having 1 to 6 carbon atoms, mercaptoalkyl having 1 to 6 carbon atoms, methylthioalkyl having 1 to 6 carbon atoms in the alkyl, aminoalkyl having 1 to 6 carbon atoms, polyhydroxyalkylaminoalkyl having the formula

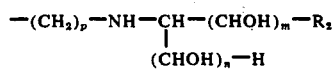

where $p$ is an integer from 1 to 6 and $m$, $n$ and $R_2$ have the following assigned values, carboxyalkyl having 1 to 6 carbon atoms in the alkyl, guanidinoalkyl having 1 to 6 carbon atoms in the alkyl, polyhydroxyalkyl-guanidinoalkyl having the formula

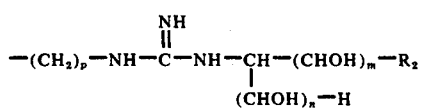

where $p$ has the above-assigned values and $m$, $n$ and $R_2$ have the following assigned values, ureidoalkyl having 1 to 6 carbon atoms in the alkyl and glyoxalinoalkyl having 1 to 6 carbon atoms in the alkyl, $R_2$ is a member selected from the group consisting of $-CH_2OH$ and —COOH, m is an integer 3 or 4, n is 0, or, when m is 3 and $R_2$ is —$CH_2OH$, n is 1, (2) alkali metal salts thereof, (3) ammonium salts thereof and (4) lower alkylammonium and lower alkylol ammonium salts thereof, and the remainder inert cosmetic excipients.

3. The composition of claim 1 wherein the pH is 6.

4. The composition of claim 2 which consists of from 5% to 15% by weight of the said at least one N-polyhydroxyalkyl-amino acid compounds.

5. The composition of claim 2 wherein the pH is 6.

6. The cosmetic moisturizing composition of claim 1 wherein said N-polyhydroxyalkyl-amino compound is the disodium salt of N-(1,3,4,5,6-pentahydroxy-2hexyl)-L-(+)-glutamic acid.

7. The cosmetic moisturizing composition of claim 2 wherein said N-polyhydroxyalkyl-amino compound is the disodium salt of N-(1,3,4,5,6-pentahydroxy-2-hexyl)-L-(+)-glutamic acid.

8. The cosmetic moisturizing composition of claim 1 wherein said N-polyhydroxyalkyl-amino compound is N-(2,3,4,5,6-pentahydroxy-hexyl)-glycine.

9. The cosmetic moisturizing composition of claim 1 wherein said N-polyhydroxyalkyl-amino compound is N-2,3,4,5,6-pentahydroxy-hexyl)-DL-alanine.

10. The cosmetic moisturizing composition of claim 1 wherein said N-polyhyroxyalkyl-amino compound is N-(2,3,4,5,6-pentahydroxy-hexyl)-DL-serine.

11. The cosmetic moisturizing composition of claim 1 wherein said N-polyhydroxyalkyl-amino compound is N-(2,3,4,5,6-pentahydroxy-hexyl)-L-(+)-aspartic acid.

12. The cosmetic moisturizing composition of claim 1 wherein said N-polyhydroxyalkyl-amino compound is N-(2,3,4,5,6-pentahydroxy-hexyl)-L-(+)-arginine.

13. The cosmetic moisturizing composition of claim 1 wherein said N-polyhydroxyalkyl-amino compound is N,N'-di-(2,3,4,5,6-pentahydroxy-hexyl)-L-(+)-arginine.

14. The cosmetic moisturizing composition of claim 1 wherein said N-polyhydroxyalkyl-amino compound is N-(2,3,4,5,6-pentahydroxy-hexyl)-L-(+)-glutamic acid.

15. The cosmetic moisturizing composition of claim 1 wherein said N-polyhydroxyalkyl-amino compound is N-(2,3,4,5,6-pentahydroxy-hexyl)-DL-threonine.

16. The cosmetic moisturizing composition of claim 1 wherein said N-polyhydroxyalkyl-amino compound is N-(2,3,4,5,6-pentahydroxy-hexyl)-DL-methionine.

17. The cosmetic moisturizing composition of claim 1 wherein said N-polyhydroxyalkyl-amino compound is N-(2,3,4,5,6-pentahydroxy-hexyl)-L-(+)-citrulline.

18. The cosmetic moisturizing composition of claim 1 wherein said N-polyhydroxyalkyl-amino compound is N,N'-di-(2,3,4,5,6-pentahydroxy-hexyl)-L-(+)-lysine.

19. The cosmetic moisturizing composition of claim 1 wherein said N-polyhydroxyalkyl-amino compound is N-(2,3,4,5,6-pentahydroxy-hexyl)-L-(−)-tyrosine.

20. The cosmetic moisturizing composition of claim 1 wherein said N-polyhydroxyalkyl-amino compound is N-(2,3,4,5,6-pentahydroxy-hexyl)-L-(+)-lysine.

21. The cosmetic moisturizing composition of claim 1 wherein said N-polyhydroxyalkyl-amino compound is N-(2,3,4,5-tetrahydroxy-pentyl)-L-(+)-glutamic acid.

22. The cosmetic moisturizing composition of claim 1 wherein said N-polyhydroxyalkyl-amino compound is N-(5-carboxy-2,3,4,5-tetrahydroxy-pentyl)-L-(+)-citrulline.

23. The cosmetic moisturizing composition of claim 1, whrein said N-polyhydroxyalkyl-amino compound is N-(5-carboxy-2,3,4,5-tetrahydroxy-pentyl)-L-( )-glutamic acid.

24. A process for the care and protection of the skin of warm-blooded animals which comprises topically applying to the skin a safe but effective amount as a moisturizing agent of a cosmetic preparation consisting essentially of an emulsion adjusted to a pH between 5 and 7 containing an emulsifier, from 2% to 20% by weight of at least one N-polyhydroxyalkylamino acid compound selected from the group consisting of (1) acids of the formula

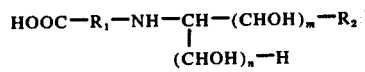

wherein $R_1$ is —$CHR_3$—, wherein $R_3$ is a member selected from the group consisting of hydrogen, alkyl having 1 to 6 carbon atoms, hydroxyalkyl having 1 to 6 carbon atoms, mercaptoalkyl having 1 to 6 carbon atoms, methylthioalkyl having 1 to 6 carbon atoms in the alkyl, aminoalkyl having 1 to 6 carbon atons, polyhydroxyalkylaminoalkyl having the formula

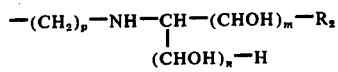

where p is an integer from 1 to 6 and m, n and $R_2$ have the following assigned values, carboxyalkyl having 1 to 6 carbon atoms in the alkyl, guanidinoalkyl having 1 to 6 carbon atoms in the alkyl, polyhydroxyalkyl-guanidinoalkyl having the formula

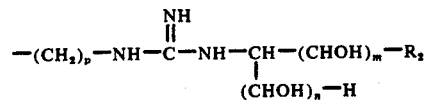

where p has the above assigned values and m, n and $R_2$ have the following assigned values, ureidoalkyl having 1 to 6 carbon atoms in the alkyl and glyoxalinoalkyl having 1 to 6 carbon atoms in the alkyl, $R_2$ is a member selected from the group consisting of —$CH_2OH$ and —COOH, m is an integer 3 to 4, and n is 0, or, when m is 3 and $R_2$ is —$CH_2OH$, n is 1, (2) alkali metal salts thereof, (3) ammonium salts thereof and (4) lower alkylammonium and lower alkylol ammonium salts thereof, and the remainder inert cosmetic excipients, said emulsion being selected fron the group consisting of oil-in-water emulsions and water-in-oil emulsions.

25. The process of claim 24 wherein said at least one N-polyhydroxyalkyl-amino acid compound is present in said cosmetic preparation in an amount of from 5% to 15% by weight.

26. The process of claim 24 wherein at last one N-polyhydroxyalkyl-amino acid compound is the disodium salt of N-(1,3,4,5,6-pentahydroxy-2-hexyl)-L-(+)-glutamic acid.

27. A process for the care and protection of the skin of warm-blooded animals comprising topically applying to the skin a safe but effective amount as moisturizing agent of a cosmetic preparation consisting essentially of a water and ethanol solution adjusted to a pH between 5 and 7 containing from 2% to 20% by weight of at least one N-polyhydroxyalkylamino acid compound selected from the group consisting of (1) acids of the formula

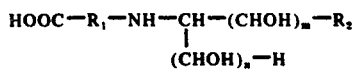

wherein $R_1$ is $-CHR_3-$, wherein $R_1$ is a member selected from the group consisting of hydrogen, alkyl having 1 to 6 carbon groups, hydroxyalkyl having 1 to 6 carbon atoms, methylthioalkyl having 1 to 6 carbon atoms, methylthioalkyl having 1 to 6 carbon atoms in the alkyl, aminoalkyl having 1 to 6 carbon atoms, polyhydroxyalkylaminoalkyl having the formula

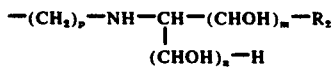

where $p$ is an integer from 1 to 6 and $m$, $n$ and $R_2$ have the following assigned values, carboxyalkyl having 1 to 6 atoms in the alkyl, guanidinoalkyl having 1 to 6 carbon atoms in the alkyl, polyhydroxyalkylguanidinoalkyl having the formula

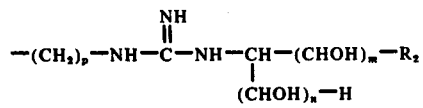

where $p$ has the above assigned values and $m$, $n$ and $R_2$ have the following assigned values, ureiodoalkyl having 1 to 6 carbon atoms in the alkyl and glyoxalinoalkyl having 1 to 6 carbon atoms in the alkyl, $R_2$ is a member selected from the group consisting of $-CH_2OH$ and $-COOH$, $m$ is an integer 3 to 4, and $n$ is 0, or, when $m$ is 3 and $R_2$ is $-CH_2OH$, $n$ is 1, (2) alkali metal salts thereof, (3) ammonium salts thereof and (4) lower alkylammonium and lower alkylol ammonium salts thereof, and the remainder inert cosmetic excipients.

28. The process of claim 27 wherein said at least one N-polyhydroxyalkyl-amino acid compound is present in said cosmetic preparation in an amount of from 5% to 15% by weight.

29. The process of claim 27 wherein said at least one-N-polyhydroxyalkyl-amino acid compound is the disodium salt of N-(1,3,4,5,6-pentahydroxy-2-hexyl-L-(+)-glutamic acid.

30. The composition of claim 1 which consists of 5% to 15% by weight of said at least one M-polyhydroxyalkyl-amino acid compounds.

* * * * *

UNITED STATES PATENT OFFICE
CERTIFICATE OF CORRECTION

Patent No. 4,032,676          Dated June 28, 1977

Inventor(s) Arnold Heins, Hinrich Moller and Rainer Osberghaus

It is certified that error appears in the above-identified patent and that said Letters Patent are hereby corrected as shown below:

| Col. | Line | |
|---|---|---|
| 1 | 32-33 | "polyhydroxalkyl quandinoalkyl" should be -- polyhydroxalkylquanidinoalkyl--. |
| 1 | 46 | "$R_2$ $_z$is" should be --$R_2$ is -- |
| 2 | 36 | "CPOOH" should be --COOH-- |
| 3 | 5 | "In" should be --If-- |
| 3 | 6 | "presemt" should be --present-- |
| 3 | 38 | "alkyl guanidinoalkyl" should be --alkyl, guanidinoalkyl--. |
| 4 | 35 | "-)+)" should be --(+)-- |
| 4 | 39 | "(+0-" should be --(+)- -- |
| 8 | 67 | "hours C" should be --hours to 50°C-- |
| 9 | 39 | "33 hours" should be --3 hours-- |
| 11 | Table I 4th Col. | "," should be -- - -- |
| 16 | 1 | "( )" should be --(+) |

UNITED STATES PATENT OFFICE
CERTIFICATE OF CORRECTION

Patent No. 4,032,676     Dated June 28, 1977

Inventor(s) Arnold Heins, Hinrich Moller and Rainer Osberghaus

It is certified that error appears in the above-identified patent and that said Letters Patent are hereby corrected as shown below:

| Col. | Line | |
|------|------|---|
| 16 | 22 | "atons" should be --atoms-- |
| 16 | 50 | "fron" should be --from-- |
| 17 | 10 | "carbon groups" should be --carbon atoms-- |
| 17 | 11 | "methylthioalkyl" should be --mercaptoalkyl-- |

Signed and Sealed this

Third Day of January 1978

[SEAL]

Attest:

RUTH C. MASON
Attesting Officer

LUTRELLE F. PARKER
Acting Commissioner of Patents and Trademarks